United States Patent
Shoenfeld

(10) Patent No.: US 7,809,470 B2
(45) Date of Patent: Oct. 5, 2010

(54) CONTROLLED ACCESS SUPPLY CABINET AND SYSTEM

(75) Inventor: Norman A. Shoenfeld, Livingston, NJ (US)

(73) Assignee: S & S X-Ray Products, Inc., Pen Argyl, PA (US)

(*) Notice: Subject to any disclaimer, the term of this patent is extended or adjusted under 35 U.S.C. 154(b) by 819 days.

(21) Appl. No.: 11/606,316

(22) Filed: Nov. 28, 2006

(65) Prior Publication Data

US 2008/0122615 A1    May 29, 2008

(51) Int. Cl.
    *G06F 17/00* (2006.01)
(52) U.S. Cl. .............. 700/243; 700/242; 700/241; 700/237; 700/232; 221/123; 221/133
(58) Field of Classification Search ......... 700/231–244; 221/99, 123, 133
    See application file for complete search history.

(56) References Cited

U.S. PATENT DOCUMENTS

| | | | | |
|---|---|---|---|---|
| 4,812,629 A * | 3/1989 | O'Neil et al. | ............... | 235/383 |
| 5,385,265 A | 1/1995 | Schlamp | .................. | 221/7 |
| 5,499,707 A * | 3/1996 | Steury | ....................... | 194/217 |
| 5,622,470 A * | 4/1997 | Schaefer et al. | ........... | 414/807 |
| 5,638,985 A | 6/1997 | Fitzgerald et al. | ........... | 221/125 |
| 5,713,270 A | 2/1998 | Fitzgerald et al. | ............. | 100/49 |
| 6,182,857 B1 | 2/2001 | Hamm et al. | .................. | 221/2 |
| 6,330,856 B1 | 12/2001 | Fitzgerald et al. | ............. | 100/52 |
| 6,393,339 B1 | 5/2002 | Yeadon | ...................... | 700/237 |
| 6,416,270 B1 * | 7/2002 | Steury et al. | ................. | 414/282 |
| 6,488,462 B1 | 12/2002 | Williams | .................... | 414/277 |
| 6,502,718 B2 | 1/2003 | Fitzgerald et al. | ........... | 221/131 |
| 6,876,902 B2 | 4/2005 | Nikolich | ..................... | 700/242 |
| 6,994,409 B2 | 2/2006 | Godlewski | ................... | 312/297 |
| 2004/0186620 A1 | 9/2004 | Chirnomas | ................... | 700/231 |
| 2006/0045674 A1 | 3/2006 | Craven | ........................ | 414/277 |
| 2006/0181234 A1 * | 8/2006 | Study et al. | .................. | 318/364 |

* cited by examiner

*Primary Examiner*—Gene Crawford
*Assistant Examiner*—Michael K Collins
(74) *Attorney, Agent, or Firm*—Bernhard P. Molldrem, Jr.

(57) ABSTRACT

An automated supplies cabinet dispenses supply items that are stored in a rack of drawers within a locking cabinet. A robotic transfer mechanism fetches the drawer containing the desired supply items, and brings it to an access portal at the front of the cabinet. A sliding door opens automatically to provide access. The supply articles can be RFID tagged and an RFID reader provides for automatic inventory updating when the articles are taken. The racks can take the form of carts that wheel into place in the cabinet. A light curtain disposed at the access portal can block movement of the door and of the transfer mechanism if it detects a hand reaching in. The cabinet provides an audit trail and facilitates inventory control and patient billing.

13 Claims, 5 Drawing Sheets

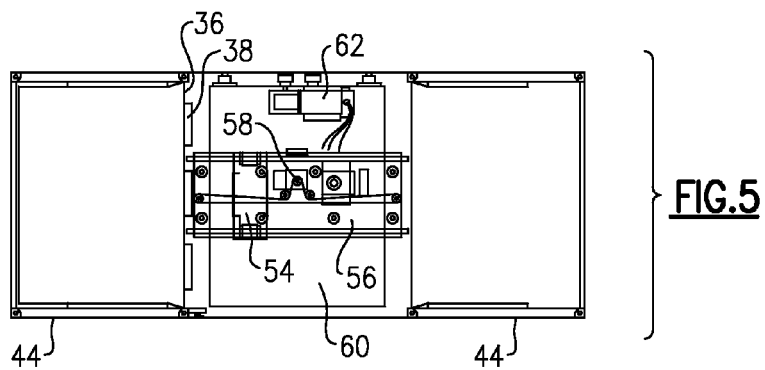
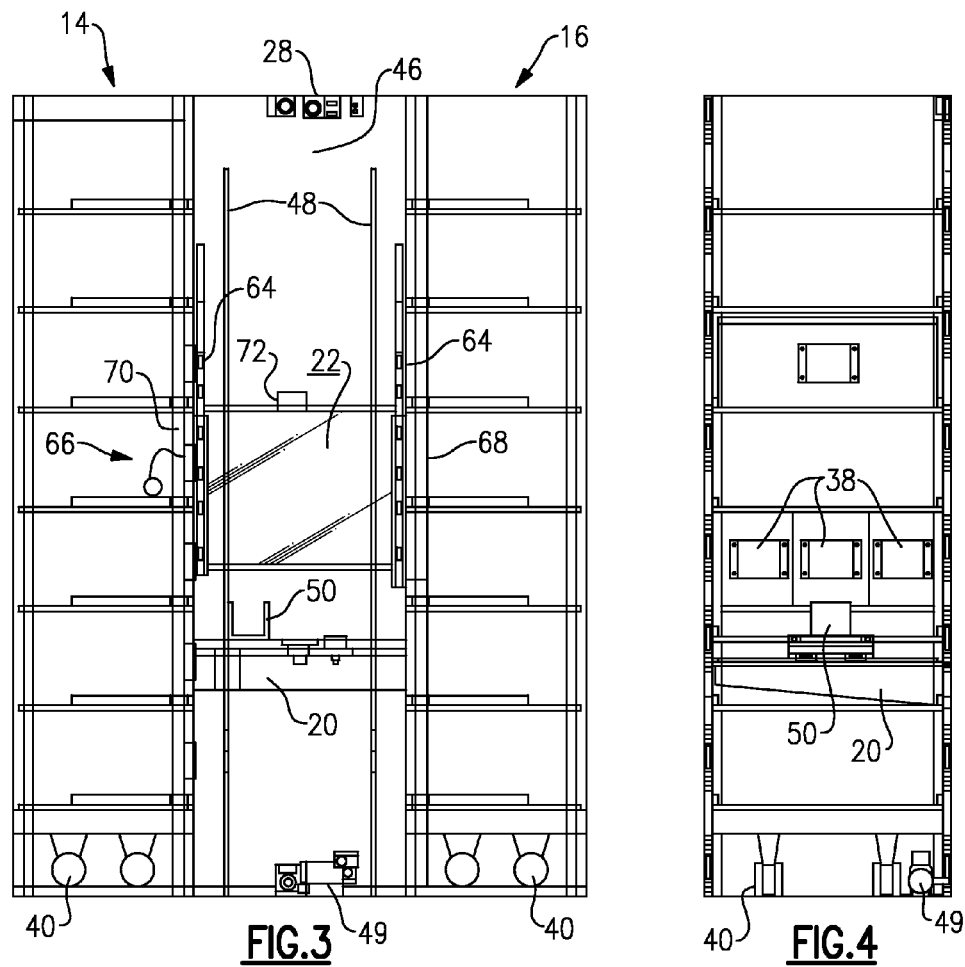

CONTROLLED ACCESS SUPPLY CABINET AND SYSTEM

BACKGROUND OF THE INVENTION

This invention relates to cabinets or storage facilities for keeping supply articles, and is more particularly directed to a system to modernize supply chain management and track inventory items. The invention is more specifically directed to a cabinet suitable for use in a hospital or health care facility, for providing controlled access to a stock of supply items such as dressings, tape, IV bags, infusion kits, gloves, masks, tissues, and personal items, and more specifically to a controlled access cabinet that facilitates keeping an audit trail of access to the various supply items stored in the cabinet.

At the present time, disposable items are routinely kept on mobile hospital carts on hospital floors. These carts are used for the type of disposable items listed above. The carts are stocked in a central supply, and wheeled up to the patient floors on a daily basis. In some facilities, the carts are kept in a locked room on the floor, with the nursing staff having to obtain the key to the room in order to access these supplies. In other facilities, the carts are kept out at the nursing station or in the hallway, providing open access for anyone to remove these items from the supply carts.

Tracking the inventory of these supply items is difficult and unreliable. The tracking of items removed from the cart, if carried out at all, has been performed using a manual system. In some facilities this involves removing stickers from the individual items, and then placing them on a patient-specific sheet, for later billing purposes. This system is highly prone to errors, as it fails to track some items altogether, leads to frequent billing errors, provides insufficient security, and does not provide the hospital or other facility with any real-time status information about the inventory levels of the supply items in the carts.

It would be desirable to employ a limited-access cabinet for disposable supply items at a convenient location on the hospital floor, which can be loaded by hospital supply staff and kept securely until needed; which will automatically keep track the items removed from the cabinet; and which can provide the hospital supply department with a real-time inventory level for these items. It is also desirable to limit access to the nursing staff and other authorized persons, and to keep an audit record of when and by whom access to the supplies was obtained.

It is also desirable that the cabinet make efficient use of floor space, and fit as much inventory into as small a footprint as possible. The supply cabinet should make it simple for authorized persons to obtain the supply items they need.

OBJECTS AND SUMMARY OF THE INVENTION

Accordingly, it is an object of the present invention to provide a controlled cabinet for disposable supply items which avoids the drawbacks of the prior art.

It is another object to provide a supply cabinet that keeps track of the inventory of the items in the cabinet and of the identity or persons accessing the cabinet as well as times of such access.

It is still another object to provide a controlled supply cabinet that is can be easily stocked by supply personnel.

According to an aspect of the invention, the supply cabinet involves a mechanism to enable secure access and inventory control over the materials supplied within it. In a favorable implementation, the supply items are stored in respective drawers from which the items can later be removed when needed. There is at least one rack of drawers, with the drawers being disposed in respective spaces that are arrayed vertically in the rack, i.e., one above the other. These drawers slide horizontally out of and into the respective spaces, and each of the drawers has a drawer pull to facilitate its being pulled out. A secure locking enclosure contains the one or more racks of drawers and its interior defines a vertical shaftway adjacent the rack(s) of drawers. A front wall of the enclosure has an access opening or door situated adjacent the shaftway.

A robotic transport mechanism moves vertically in this shaftway for fetching a selected one of said drawers, i.e., the drawer containing the needed supply articles. The transport mechanism brings the drawer to the access opening, where the authorized person can remove the item(s) from the drawer. Thereafter the robotic transport mechanism returns the drawer to the level of its respective space in the rack, and pushes it back into its assigned space.

Favorably, the transport mechanism has a platform, i.e., elevator, disposed for vertical movement in the shaftway. The platform may be slidable along a set of vertical rails or runners.

A hook or finger or probe on the platform serves as a gripping mechanism that grasps the drawer pull of the selected drawer to pull the drawer out of its space in the rack. This is mounted on a movable carriage and a drive mechanism moves the carriage and the gripping mechanism laterally to draw the drawer out from its respective space in the rack, and thereafter moves these elements in the other direction to push the drawer back into its space on the rack. The platform includes slides, rollers or another equivalent mechanism for slidably supporting the drawer on the platform.

A control processor in the cabinet responds to requests for access and directs the platform to carry out controlled raising and lowering the platform and drawer. This processor or an associated processor stores the identity of the contents of each drawer and the location of the respective space on the rack or racks for each drawer. The cabinet thus automatically directs the transport mechanism to the selected drawer, and causes the transport mechanism to bring the drawer from its respective space in the rack, present the selected drawer at said access opening, and thereafter return the drawer to its space in the rack.

In many preferred embodiments, there is a vertically movable sliding door at the access opening, including means for automatically opening and closing the sliding door for access to the drawer when it is brought to the access opening. The cabinet may also employ a light curtain disposed at the access opening, and this may include a light transmitter at one side of the access opening and a receiver arrangement situated at an opposite side of the access opening to detect a break in the light received from said light transmitter. These are incorporated with the control processor for disabling movement of the transport mechanism when such a break is detected. This arrangement may also disable movement of the vertical sliding door when a break in the light received at the light receiver arrangement is detected.

To facilitate loading of the inventory, i.e., stocking the supply items, the rack of drawers can preferably be configured as a cart having wheels, permitting the rack to be moved by rolling it. In this case, the cabinet enclosure includes a locking door that permits the cart to be rolled into place in the cabinet. This way, hospital supply personnel can load the cart and bring it up to the location of the cabinet, bring the empty or partly emptied cart out, wheel the loaded cart into place, and close up the cabinet. Then the emptied cart is simply returned to the supply room for restocking. In a preferred version of the cabinet, two racks or carts are situated within the cabinet, and disposed facing one another on left and right sides of the shaftway i.e. the robotic transport mechanism. The two mobile racks or carts are filled in the central supply area of the hospital. The two carts can be "piggybacked" i.e., strapped or clamped together and wheeled up to the nursing units. Then the carts can be separated from one another and wheeled into the secure cabinet enclosure.

An RFID reader is also located at the access door, to track which articles have been removed. In this case, the articles in the drawers are have RFID chips attached. The RFID reader is situated at the access door and this is coupled to the on-board processor to make it possible to detect and identify items that are taken.

The system also provides for computer based automated access, such that a nurse or other authorized person can actuate the robotic transport mechanism. This system can involve a touch-screen computer mounted on the cabinet or on a wing attached to the cabinet, or can involve a hospital computer at the nurse station connected e.g. either wirelessly or via a USB port with the controller in the cabinet. The cabinet can also be accessed remotely, e.g., via the hospital supply computer using the hospital computer network.

Cabinets such as this can be employed in environments outside the hospital supply application described here. For example, these cabinets can be used in automotive repair or manufacturing for controlled access to parts and supplies. The cabinets may also be used in hotel and similar applications for room supplies, towels, or the like. The cabinets may be constructed as furniture also for home use, whereby a person may store clothing, i.e., as a stand alone or networked dresser or chest. In each case, because the robotic transport provides access to high drawers that would otherwise be inaccessible, the storage available is increased approximately three times that of a standard dresser.

When used as a dresser or similar application, the drawers can be identified by function when the arrangement is set up, i.e., either by intended contents (socks, underwear, pajamas, etc.) or by day of week, where a different outfit can be stored in each drawer.

In each case, the drawers can be password protected, to limit access. Different drawers may have different passwords, i.e., so that they may be associated with different users. The contents of the drawers can be monitored, i.e., the inventory of stock can be tracked, with possible notifications of when it is time to do a wash. This may occur e.g. when socks or underwear inventory drops below some preset level. Where the cabinet is associated with a PC or other computer, an email notification can be automatically sent to the user, or to the user's wife, mother or caretaker.

In the application as a dresser, the drawer racks may be fixed in place, rather than configured as wheeled carts.

In the hospital supply cabinet configuration, the nurses or other authorized hospital personnel are provided with an access code, password, or an access device such as mag stripe card, bar-coded badge, or RFID card or badge. The cabinet is kept locked to control access.

When a nurse wants to access the cabinet for supplies for a given patient, she or he first enters a personal password or access code. This may be done by entering an alphanumeric password using a keyboard or touchscreen, or by fingerprint identification, or by scanning his or her ID badge, or by detecting a personal RFID chip on his or her badge. Then, the nurse enters the patient's name, ID number, or room number. This may be accomplished using a drop-down menu on the PC or LCD touch screen, or by scanning the patient's barcode or room barcode. Then the needed supply items can be selected, e.g., from a drop-down menu on the screen. This menu may be automatically populated from barcode or RFID information on the carts or drawers themselves, or from information stored in the central supply computer, regarding what contents are actually stocked in the drawers of each individual mobile cart. This information may be accessed over the hospital network. In addition, the supplies previously used for this patient may be again displayed, as a means of accelerating the selection process.

The dispensing cabinet (or perhaps a series of cabinets) then automatically select the drawers in which the particular articles are stored, and brings the drawers to the front at the centrally located dispensing door, i.e., access opening, and the sliding door automatically opens. Then, the nurse removes the items. This may involve a secondary scanning such as by RFID chips carried on the articles.

Meanwhile, in the process of dispensing, there is an audit trail created in background. The audit trail identifies who opened the cabinet, at what time, and what items were accessed. This is important for security—if inventory counts are found to be incorrect during or at the end of the day, a record as to who entered the specific drawers can be used to investigate the error. The fact that it is known that a record is being kept will reduce the incidence of errors and reduce the inventory shrinkage, i.e. the number of items disappearing from the floor.

A record of what items were removed from the cabinet for each individual patient is recorded, and can be used for correct billing capture. This information can be obtained from the list of items with quantities as selected by the nurse, and confirmed by barcode or RFID scanning of the items as they are removed from the cabinet. Alternatively, if an RFID-based inventory is kept, the difference in inventory noted within each cabinet will accurately identify what items were removed for the selected patient.

Real-time inventory can be monitored from central supply. Shortages that occur between scheduled replenishment times can be identified and corrected before these shortages become emergencies. Similarly, if few supplies were accessed from a given cabinet, the scheduled trip for cart exchange or restocking can be postponed to a later time, eliminating unnecessary trips. The levels of acceptable inventory, restock levels, and warning levels can be individually programmed in the main inventory software, and notifications can be performed using email messaging or pop-up notifications.

The audit trail also keeps track of the times the carts are accessed for restocking purposes.

The controlled access supply cabinet features left and right sided locking doors to accept tall mobile carts on each side of the central robotic transport mechanism. The access portal or opening is centrally located at a convenient height, so it is easy to reach in without the nurse having to bend or stretch. The central robotic transport mechanism moves to the selected drawer, fetches the drawer, and brings it to the front of the cabinet and places it at the access port or opening.

In the medical supplies cabinet, the racks of drawers are configured as two tall mobile carts, disposed to the left and right, and are designed to be clamped together for secure transport to the floor from the hospital supply room. The mobile carts have multiple shelves or positions for the drawers, and can have multiple drawers per shelf. The carts have an increased capacity, with drawers down close to the floor and going up to the ceiling, to a height of six feet or higher. The robotic transport mechanism permits easy access to the less accessible locations, i.e., the very low and very high drawers. When the two carts are clamped together for transport, access to the drawers is not permitted.

The ability of the robotic transport mechanism to reach the high shelves and bring the contents down to a convenient access opening allows increased functional storage, limited only by ceiling height in the room where the cabinet is located.

The option of automatic barcode or RFID reading permits self-calibration and set-up of the cart, i.e., to identify the location of the drawers, how many drawers per shelf, height of the drawers, and content of each of the drawers. The cabinet may be connected via USB (or serial port, Firewire, Ethernet or other system) to local networked computer or computers. Multiple cabinets in the same supply area can be networked to the same local PC, which can then control access and inventory simultaneously for multiple cabinets. These can also be sued to scan items removed from the cabinet as a secondary check.

Optionally, individual cabinets can be controlled using a local touchscreen mounted onto the front of the cabinet, to control access and to record the audit trail.

There can be a manual unlock provision, so that in the event of a power or device failure, supply items can be removed from the cabinet by manually unlocking the left and right doors, and removing the carts. The supplies then can be scanned by the local PC to create the audit trail, if the local PC is receiving normal power or battery power. Otherwise, the audit trail can be maintained by manual methods.

In one preferred configuration, the supply items are all provided with RFID tags or labels, and the cabinet can automatically sense the current inventory based on the signals from these devices. The RFID reader identifies the items passing through the access opening. After the cabinet is accessed, the cabinet can again take its own inventory based on these RFID signals. Anything that has been removed can be charged to the patient for whom the cabinet was opened. This eliminates the need to rescan barcodes on the items removed, and makes inventory counts independent of the number of items scanned-in when the items are taken. The cabinet can similarly recheck inventory upon being re-stocked. An RFID-based system at the supply center can be employed for automatically identifying the items when restocking the individual drawers in the carts.

With the automated, controlled access cabinet of this invention, a local PC can be connected to one or to multiple cabinets, and also networked to the central supply computer. The main PC in the materials management office can be networked to the series of remote supply cabinets. There may be an excess of carts, so that the carts can be re-loaded or re-stocked in central supply and then simply brought up to the hospital floor and swapped for the carts that had been installed previously. The loading of the carts is networked to the central supply PC.

Software on the main supply computer can have these functionalities, as well as others: Keeping track of real-time inventory in each mobile cart and in each supply cabinet. The system also maintains an audit trail of who enters the cabinet, the patient for whom the supplies were removed, what supply items were removed for that patient, and the time that the supply items were removed. The system also maintains a list of the accepted ID's for the authorized personnel, i.e., alphanumeric passwords, RFID codes, fingerprints, etc., both for cart access and to update the local PC with the select list of ID's for any one particular cabinet or group of cabinets.

The software also allows specification of acceptable inventory, replacement levels, and emergency replacement levels for specific types of supply items or other inventory items, and provides flags to the user when replacement or emergency level situations exist. These flags may be emails or pop-up notifications, for example.

Patient supply usage data can be exported to the hospital billing system. Reports of usage, audit trail, inventory levels, restocking times for individual cabinets are created either on a scheduled basis or in real time. Specifications can be made for reorder points for different supply items, and the software can then generate an automatic notification to the supplies or materials manager. Alternatively, or in addition, an email message can be automatically generated and sent to the purchasing department when a specified quantity of a given inventory item has been dispensed.

The cabinet may employ a touch screen computer monitor mounted, e.g., in a VESA mount incorporated into the front wall of the cabinet enclosure to serve as automatic access facility. The nurse or other authorized person can enter a pass code and identification onto soft keys on the touch screen, or through other means such as a card swipe card reader, an RFID receiver, fingerprint scanner or other similar means for identifying the care giver for access. The touch screen computer monitor may be part of a PC computer or may connect with a unit inside the cabinet. Alternatively, the cabinet may have a small touchscreen display. The PC may employ a network interface for connecting with a hospital computer network, so that the locked drawers can be opened remotely via the hospital computer network. Access to the cabinet drawers can be achieved using a wireless hand-held device, e.g., a wireless Palm Pilot. This can employ Wi-Fi, infrared, or blue tooth technology.

The above and many other objects, features, and advantages of this invention will become apparent from the ensuing description of a selected preferred embodiment, which is to be considered in connection with the accompanying Drawing.

BRIEF DESCRIPTION OF THE DRAWING

FIG. 3 is a front elevation showing the carts and robotic transport mechanism of this invention.

FIG. 4 is a side elevation of this embodiment.

FIG. 5 is a top plan view, showing the robotic transport mechanism in the enclosure according to this embodiment.

DETAILED DESCRIPTION OF THE PREFERRED EMBODIMENT

Figure 1:
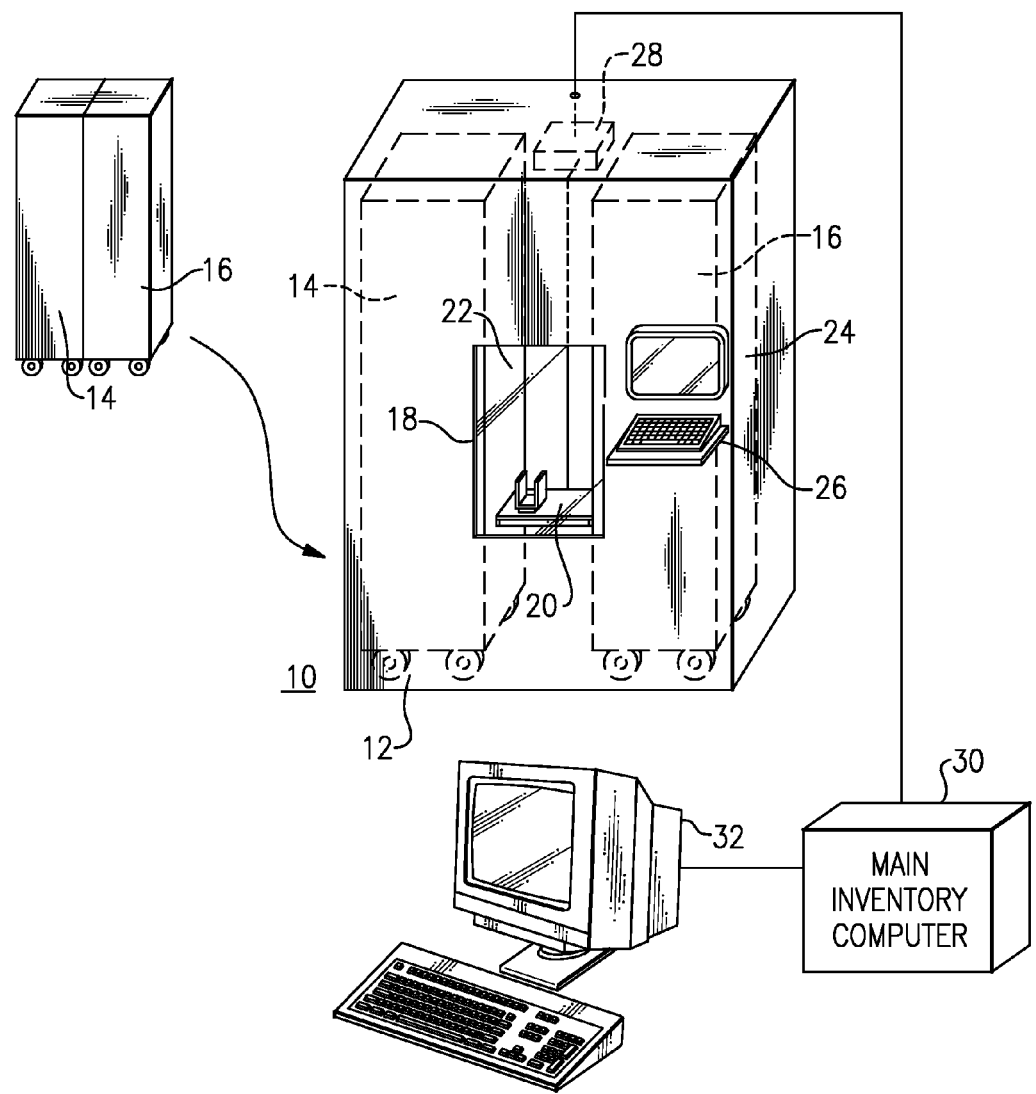
FIG. 1 is a schematic view of a network-connected system including a hospital supplies cabinet(s) according to one preferred embodiment of this invention.
Figure 2:
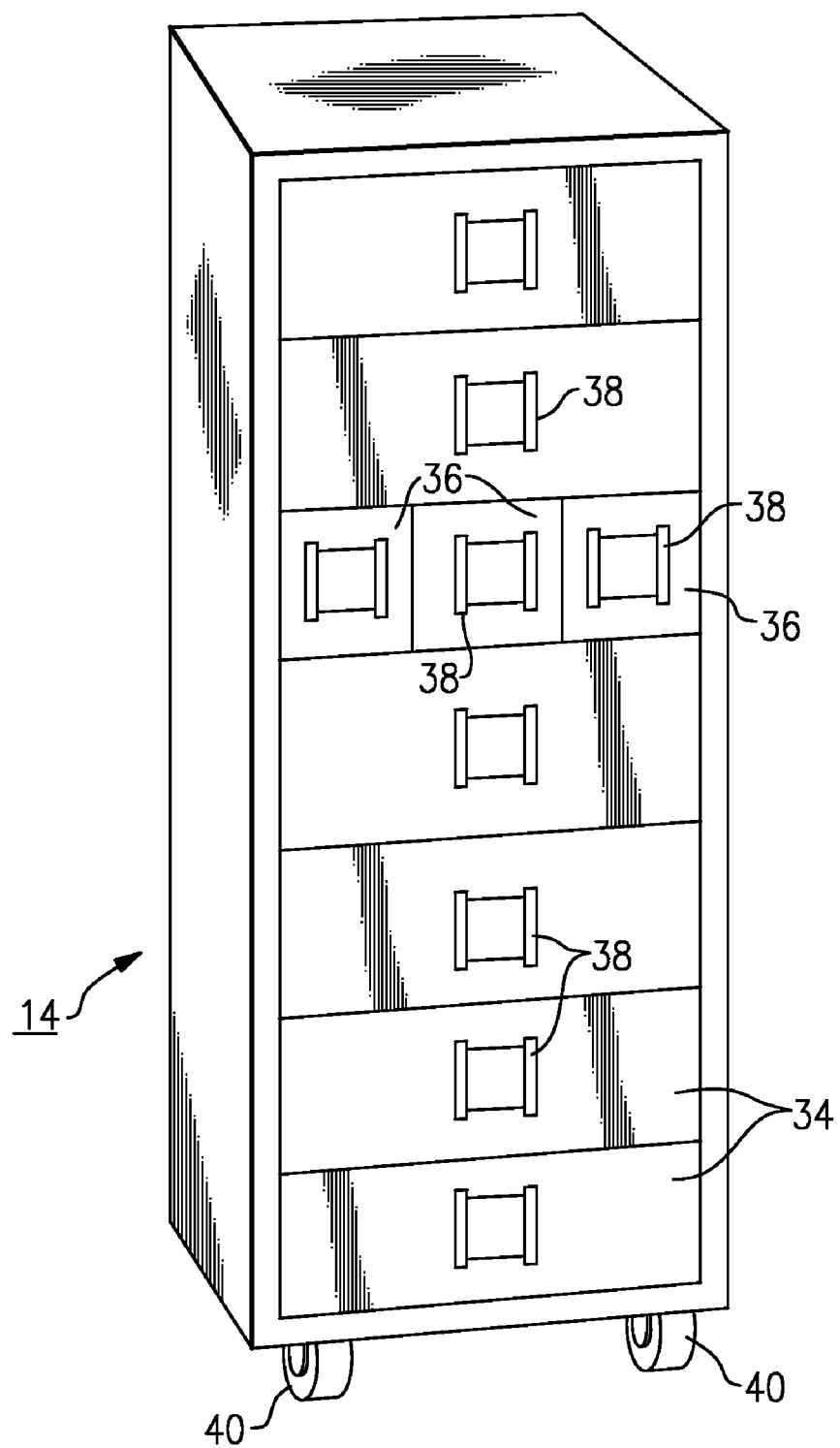
FIG. 2 is a perspective view of a rack of drawers in the form of a cart according to this embodiment.

With reference to the Drawing, and initially to FIGS. 1 and 2, a robotic dispensing supply cabinet 10 for a hospital or other health care facility has a secure locking cabinet enclosure 12, with wheeled carts 14 and 16 situated on left and right sides within the enclosure 10. The carts are in the form of racks of drawers, with the drawers arranged vertically, and with the drawers facing one another across a central zone, i.e. an open shaftway. There is an access opening or portal 18 on the front wall. A robotic transport mechanism 20 is situated in the shaftway space between the two carts 14, 16. The transport mechanism is configured to move vertically along vertical guide rails to align with the level of a selected drawer on one of the carts, and then automatically pull out the selected drawer from the cart and bring the drawer down to a position at the access portal 18. A sliding door 22 is situated at the opening or portal 18. This door is normally closed, but opens when the robotic transport mechanism has fetched the selected drawer and brought it into position at the access portal 18. In this embodiment, the door 22 is shown to be transparent, but need not be in other embodiments.

In this embodiment, there is a touch screen monitor 24 and associated computer situated on one front wall of the cabinet 10. This monitor 24 can be the device where the nurse or other authorized person enters a password to access the cabinet. The monitor can also provide a sequence of pull-down menus to permit the nurse to select a particular supply item, i.e., gown, gloves, bandage, etc., and to identify the associated patient. A keyboard 26 or other entry device can also be mounted on the cabinet or on a panel near the cabinet to provide a means for password entry and entry of other data. This device may also include a fingerprint reader, magnetic card swipe device, bar code scanner, etc., to identify the authorized user obtaining access. The monitor 24 and/or keyboard 26 can be mounted on one side or on the front of the cabinet 10, or can be on a separate panel or wing of the unit. Alternatively, access can be obtained from another computer device or from a network, using a USB or other cable connection or using a wireless connection.

An internal digital controller 28 is shown installed near the top of the cabinet. This is programmed to track the contents of each drawer on each cart and to control access and control movement of the robotic transport mechanism 20 and the sliding door 22.

The controller 28 is connected (by cable, network, or wirelessly) to a main supply inventory computer, which is located at the hospital supply facility. Here, a keyboard and monitor 32 are used to monitor the activity of all the cabinets 10 located throughout the hospital. The main supply inventory computer also tracks inventory levels and keeps an audit record of access for each of the cabinets. This computer 30 also relays billing information (i.e., accounting which supplies were taken for which patient) to a main hospital billing computer, and can automatically notify the purchasing department when inventory levels for given inventory items drop below some predetermined threshold.

As also shown in FIG. 1, a pair of these carts 14, 16 can be clamped or strapped together at the supply center after being loaded, and the two carts 14, 16 are then wheeled together to be installed in the cabinet enclosure 12. The carts are clamped with the drawers facing the drawers of the other cart, so that the drawers cannot be accessed during transport.

As shown in FIG. 2, the cart 14 or 16 is configured as a rack of drawers 34, each drawer at a respective location and being situated one over the other, so the drawers 34 are in a vertical array. The cart 14 has corresponding shelves or spaces, with drawer slides as appropriate, so that the drawers 34 can be drawn out and then can slide back in to the respective location. In some cases, there can be plural drawers at a single level, and here at one location there are three drawers 36, each one-third the width of the other, full-size drawers 34. These drawers 36 can be used for smaller items. Each drawer 34, 36 has a drawer pull 38 at a center of its front panel, which permits a hook or pulling device to reach behind it and pull out the associated drawer 34 or 36. Here, each drawer pull 38 is open at the bottom to permit insertion of a hook member located on the robotic transfer arrangement 20, as will be discussed later. Each rack rests on wheels or rollers 40.

FIGS. 3, 4, and 5 show details of the enclosure 12, and carts 14 and 16, as well as the robotic transport mechanism 20

The enclosure 12 is provided with locking doors 44 (seen from the top in FIG. 5) which open to allow the carts 14, 15 to be wheeled in. Between the two carts is an open vertical shaftway 46, where the robotic transport mechanism 20 is located. Here there are vertical guide rails 48 situated in the shaftway, and the transport mechanism 20 travels up and down on these. A motor drive 49 is situated at the base of the cabinet for moving the transport mechanism. This motor drive assembly may employ belt drive, chain drive, screw drive or other means.

Shown on the transport mechanism is a transversely movable hook member 50, which comprises two vertical fingers 52, 52. The hook member slides to left and right on the transport mechanism, to position one or the other vertical finger 52 behind the drawer pull 38 of one of the drawers, and then moves to extract the drawer from the cart 14 or 16. The hook member 50 moves in the other direction to replace the drawer into its respective location on the cart.

FIG. 4 shows one of the vertical fingers 52 reaching into a gap behind the drawer pull 38 of one of the smaller drawers 36.

As shown in FIG. 5, the hook member 50 is mounted on an upper carriage 54, which slides along transverse tracks on a second carriage 56. A drive mechanism 58, which can be a belt drive, moves the carriage 54 and hook member 50 laterally. The second carriage 56 is slidably mounted on a base 60 of the robotic transport mechanism 20, and there is another drive mechanism 62 to move the second carriage 56 proximal-distally, i.e., in the front to back direction. All the drives are automatically and digitally controlled by means of the cabinet internal controller 28. Details of the transport mechanism are illustrated in more detail in FIGS. 9 and 10, and will be discussed later.

The vertically sliding door 22 is mounted on elongated slide members 64 that are oriented vertically and positioned behind the access opening 18. The sliding door 22 is normally kept in a closed, i.e., lowered position, and opens automatically after the selected drawer 34 or 36 is brought to an access position aligned with the access opening 18.

A light curtain 66 is positioned at the access port or opening 18, and includes a transmitter 68 situated at one side and a light receiver 70 at the other side. The light curtain detects if a beam of light has been broken, such as from someone's hand reaching in through the access opening, and then automatically stops action of the robotic transport mechanism 20 and the door 22. Instead of a light curtain, other equivalent mechanisms could be used to detect if the opening is penetrated.

An RFID reader 72 is positioned at the access opening as well, here at the top edge of the access opening 18. This is used to identify articles being removed from the cabinet. In this implementation, each supply article in each drawer would be provided with an RFID tag. As each article is taken and removed through the opening 18, the RFID reader 72 reads the embedded code, and transmits that via the controller 28 and the hospital network to the inventory computer 30, so that inventory levels can be tracked in real time.

Figure 6:
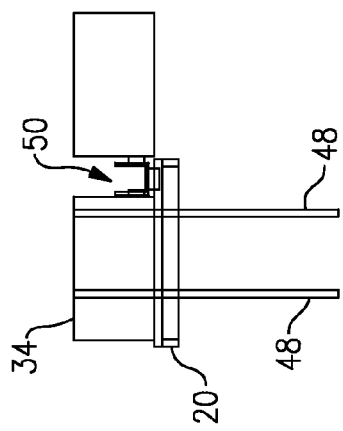
FIGS. 6, 7 and 8 are schematic views for explaining the operation of the transport mechanism of this embodiment.
Figure 7:
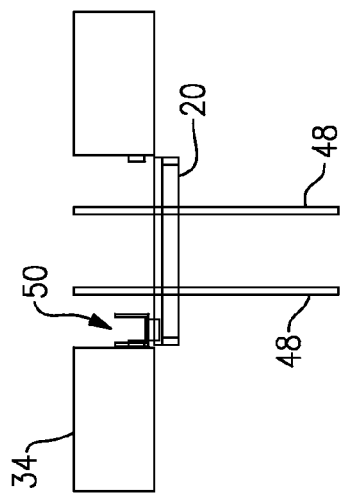
Figure 8:
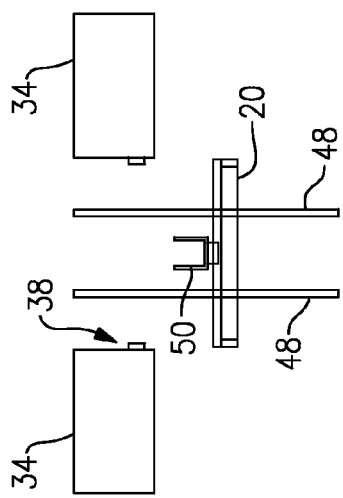

The action of the robotic transport mechanism 20 can be explained with reference to FIGS. 6, 7 and 8. When an authorized person accesses the supply cabinet 10 and requisitions a particular supply item, the robotic transport mechanism 20 moves vertically along the rails 48 to a position below the target drawer 34 where the supply items are located, as generally seen in FIG. 6. Then, the hook member 50 is moved towards the target drawer 34 (here, leftward) until it is just beneath the door pull 38. The transport mechanism 20 moves up slightly to engage the hook member behind the door pull, as in FIG. 7. Then the drive for the carriage of the hook member 50 moves the hook member 50 rightward to extract the drawer 34, as shown in FIG. 8. At this point, the drawer is supported on the transport mechanism, and is drawn completely out of the associated rack or cart. The transport mechanism 20 moves downward (or upward, as appropriate) to position the drawer at the level of the front access opening, and the drawer is moved forward, i.e., towards the opening. Then the door 22 is lifted to provide access to the drawer contents. After that, the door 22 closes, and the above process is reversed to replace the drawer into its respective place in the appropriate rack or cart.

Figure 9:
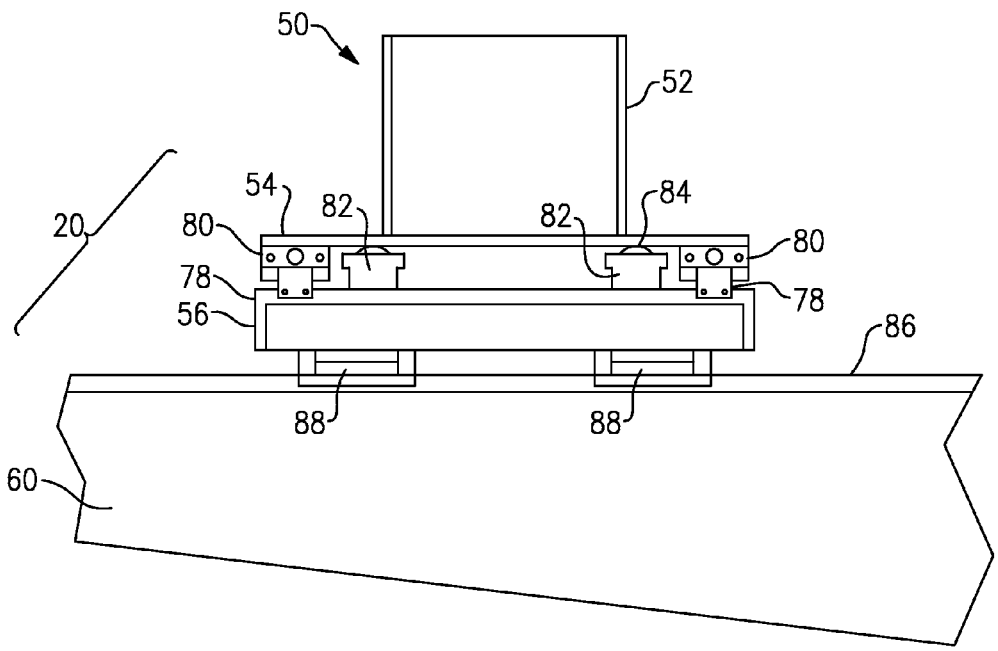
FIGS. 9 and 10 are elevation and plan views of the robotic transport mechanism of this embodiment.
Figure 10:
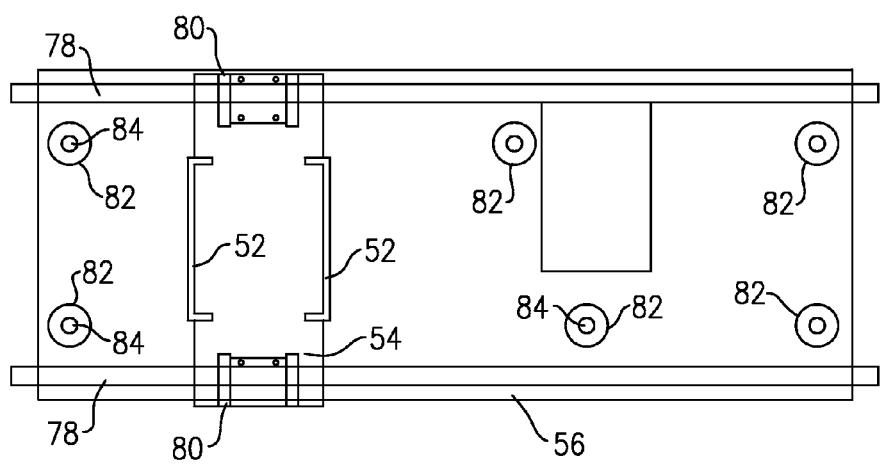

Details of the transport mechanism 20 of this embodiment are shown in FIGS. 9 and 10. The hook member 50 is shown having two vertical fingers 52, each in the form of a flat plate member. One of these fingers 52 is used to engage the drawers on the left side cart 14 and the other to engage the drawers on the right side cart 16. The hook member 50 is affixed onto the upper carriage 54. Transverse rails 78 on the second carriage 56 slidably support bearings 80 on the underside of the upper carriage 54. There are roller guides 82 arrayed on the upper surface of the second carriage, as shown. These roller guides 82 ease the movement of the drawers 34 or 36. Each roller guide is in the form of a flanged roller disposed on a vertical axis, and each has a ball 84 on its upper surface. The bottom of the drawer rides on the balls 84 of these roller guides.

There are also guide rails 86 disposed in the fore-and-aft direction on the base member 60 of the transport mechanism, and on these are journaled sliding bearings 88 that support the second carriage 56, permitting front and back movement.

An alternative arrangement, e.g., in a physician's office, can have a smaller free standing cabinet to store bandages, wipes, and other disposable or consumable articles and dispense them as needed. The smaller cabinet may have a single rack or cart, with the robotic transport mechanism situated in a shaftway to one side of the rack. An on-board computer can contain programming and memory to keep an audit trail of the times of access to each drawer and the person accessing the drawer, as well as the articles removed.

The touch-screen computer may have an active screen monitor and a thin CPU or PC mounted directly behind it. This thin PC contains the electronics, memory drives, and interfaces to operate the cabinet.

The cabinet may also have a USB cable or, alternatively, an ethernet cable or equivalent connection, extending from a USB interface, ethernet interface, or the like within the cabinet, and may connect, either by wire or wirelessly, with the hospital computer network or LAN.

While not shown here, the cabinet can favorably be provided with a key lock to permit authorized personnel to open the cabinet enclosure 12 manually (with a key) in the event a power failure, network outage, or other event that might preclude obtaining electronic access. Then, the supply items can be removed directly from each cart.

In a preferred embodiment, the hospital computer system keeps track of the times each supply cabinet 10 is accessed, and the of identities of authorized personnel who obtain (or attempt to obtain) access, and the items that have been removed, so that the system creates an audit trail of health providers who request access.

While the invention has been described hereinabove with reference to selected preferred embodiments, it should be recognized that the invention is not limited to those precise embodiments. Rather, many modification and variations would present themselves to persons skilled in the art without departing from the scope and spirit of this invention, as defined in the appended claims.

I claim:

1. A controlled supply cabinet arrangement in which supply items are stored in respective drawers from which said items can later be removed by a user without removing the respective drawer from the supply cabinet, comprising
at least one rack of drawers, said drawers being disposed in respective spaces that are arrayed vertically in said rack; said drawers being slidable horizontally out of and into the respective spaces, and each of said drawers having a drawer pull thereon, each of said drawers containing at least one of said supply items;
a secure locking enclosure in which said rack of drawers is disposed, and having an interior defining a vertical shaftway adjacent said rack of drawers; the enclosure having a front wall with an access door therein, the access door being situated adjacent said shaftway and alongside said at least one rack; wherein each of said at least one rack of drawers is configured as a cart having wheels permitting the rack to be moved by rolling it horizontally into and out of said secure locking enclosure; and wherein said enclosure includes a locking door that permits the cart to be rolled horizontally into place therein;
a transport mechanism movable vertically in said shaftway for fetching a selected one of said drawers, bringing the drawer to the access door where the user can remove one or more of said supply items from said drawer, and thereafter returning the drawer to its respective space in the rack; the transport mechanism including
a platform disposed for vertical movement in said shaftway;
grip means on said platform for grasping the drawer pull of the selected drawer;
means for moving the grip means to draw the drawer out from its respective space in the rack, and thereafter pushing the drawer back into such space;
means slidably supporting the drawer; and
means for controllably raising and lowering the platform and drawer; and
a processor storing the identity of the contents of each said drawer and the location of the respective space for each said drawer, including control means for automatically directing the transport mechanism to the selected drawer, and causing the transport mechanism to bring the drawer from its respective space in the rack, present the selected drawer at said access door, and thereafter return the drawer to its space in the rack.

2. The controlled supply cabinet arrangement according to claim 1, wherein said supply items in said drawers are fitted with RFID devices, and said controlled supply cabinet arrangement further comprising an RFID reader situated at said access opening and coupled to said processor for detecting and identifying the supply items that are taken from said selected drawer and removed through said access door.

3. A controlled supply cabinet arrangement according to claim 1 further comprising means associated with said processor for requiring entry of an access code to identify persons authorized access to the cabinet, and requiring entry of said access code before actuating said transport mechanism.

4. A controlled supply cabinet arrangement according to claim 1 comprising network interface means addressable to said cabinet to permit a networked computer to control access to a plurality of cabinets.

5. A controlled supply cabinet arrangement in which supply items are stored in respective drawers from which said items can later be removed without removing the drawer from the cabinet, comprising at least two racks of drawers, said drawers each being adapted to contain at least one supply item, and said drawers being disposed in respective spaces that are arrayed vertically in each of said racks; said drawers being slidable horizontally out of and into the respective spaces, and each of said drawers having a drawer pull thereon;

a secure locking enclosure in which said racks of drawers are disposed, the racks being situated facing one another and defining a vertical shaftway between the racks and adjacent said racks of drawers; the enclosure having a front wall with an access door therein, the access door being adjacent and alongside said shaftway;

a transport mechanism movable vertically in said shaftway adapted for fetching a selected one of said drawers from either of the racks of drawers that are facing each other adjacent said shaftway, bringing the drawer to the access door, and thereafter returning the drawer to its respective space in the respective rack; the transport mechanism including a platform disposed for vertical movement in said shaftway;

grip means on said platform for grasping the drawer pull of the selected drawer from either of said racks;

means for moving the grip means to draw the drawer out from its respective space in the rack, and thereafter pushing the drawer back into such space;

means slidably supporting the drawer; and means for controllably raising and lowering the platform and drawer; and a processor storing the identity of the contents of each said drawer and the location of the respective space for each said drawer, including control means for automatically directing the transport mechanism to the selected drawer, and causing the transport mechanism to bring the drawer from its respective space in the rack, to present the selected drawer at said access door, and thereafter to return the drawer to its space in the respective rack.

6. The controlled supply cabinet arrangement according to claim 5, wherein each said rack of drawers is configured as a cart having wheels permitting the rack to be moved by rolling it horizontally; and wherein said enclosure includes a locking door that permits the cart to be rolled into place therein.

7. The controlled supply cabinet arrangement according to claim 5, comprising a touch screen access computer mounted thereon.

8. The controlled supply cabinet arrangement according to claim 5, comprising means connecting said processor to a main supply computer.

9. The controlled supply cabinet arrangement according to claim 8, wherein the supply items in said drawers are fitted with RFID devices, and said controlled supply cabinet arrangement further comprising an RFID reader situated at said access opening and coupled to said processor for detecting and identifying the supply items that are taken from said selected drawer and removed through said access door, the RFID reader being coupled via said processor to said main supply computer, thereby to furnish continuously updated data concerning the contents of the supply cabinet arrangement.

10. The controlled supply cabinet arrangement according to claim 5, further comprising a light curtain disposed at said access opening, and including a light transmitter at one side of the access opening, a receiver arrangement situated at an opposite side of said access opening to detect a break in the light generated at said light transmitter, and means for disabling said transport mechanism when such break is detected.

11. The controlled supply cabinet arrangement according to claim 5, further comprising means for detecting the presence of an object penetrating said access opening, and means for disabling the transport mechanism during any time that such penetration is detected.

12. The controlled supply cabinet arrangement according to claim 11, comprising a vertically movable sliding door at said access opening, including means for automatically opening and closing said sliding door, and means for disabling movement of said vertical sliding door when penetration is detected.

13. The controlled supply cabinet arrangement according to claim 5, wherein said transport mechanism comprises a set of vertical rails that guide said platform vertically in said shaftway, said platform includes a set of transverse guides, a carriage that travels slidably thereon, with said grip means being mounted on said carriage and adapted to pull out and push in the drawers in either of said racks that face one another on either side of the shaftway, and drive mechanism for controllably moving said carriage on said transverse guides.

* * * * *